(12) United States Patent
Hu et al.

(10) Patent No.: US 7,634,055 B2
(45) Date of Patent: Dec. 15, 2009

(54) METHOD AND DEVICE FOR SECURITY-INSPECTION OF LIQUID ARTICLES WITH RADIATIONS

(75) Inventors: Haifeng Hu, Beijing (CN); Yuanjing Li, Beijing (CN); Kejun Kang, Beijing (CN); Zhiqiang Chen, Beijing (CN); Yinong Liu, Beijing (CN); Yulan Li, Beijing (CN); Li Zhang, Beijing (CN); Wanlong Wu, Beijing (CN); Ziran Zhao, Beijing (CN); Xilei Luo, Beijing (CN); Bin Sang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 232 days.

(21) Appl. No.: 11/634,330

(22) Filed: Dec. 5, 2006

(65) Prior Publication Data
US 2008/0056443 A1 Mar. 6, 2008

(30) Foreign Application Priority Data
Sep. 5, 2006 (CN) .................. 2006 1 0127652

(51) Int. Cl.
*G01B 15/02* (2006.01)
*G01N 23/04* (2006.01)
(52) U.S. Cl. .................................................. 378/53
(58) Field of Classification Search .......... 378/4, 378/5, 9, 15, 16, 19, 51, 53, 57, 210, 901
See application file for complete search history.

(56) References Cited
U.S. PATENT DOCUMENTS
4,035,647 A * 7/1977 Hounsfield et al. ............ 378/19
4,663,711 A * 5/1987 Vinegar et al. ................. 702/12

6,026,171 A 2/2000 Hiraoglu et al. ............. 382/100

(Continued)

FOREIGN PATENT DOCUMENTS
CN 1319759 10/2001

(Continued)

OTHER PUBLICATIONS
"International Search Report" for PCT/CN2006/003327.

(Continued)

*Primary Examiner*—Edward J Glick
*Assistant Examiner*—Anastasia Midkiff
(74) *Attorney, Agent, or Firm*—Westman, Champlin & Kelly, P.A.

(57) ABSTRACT

Disclosed is a method and a device for security-inspection of liquid articles with radiations, which relate to the field of radiation inspection technology. The method comprises steps of acquiring original environment information, emitting radiation beams to transmit the liquid articles, receiving the radiation beams transmitted through the liquid articles to form multi-angle projection data, computing a radiation absorption coefficient of the liquid articles to be detected by inverse operation of the multi-angle projection data, based on the initial environmental information and the uniformity of the liquid articles, and comparing the radiation absorption coefficients with the preset data to get the relevant information of the liquid articles. Comparing with the prior art, the present invention is not subjected to affection of cuter package of the liquid article, and is advantageous of high anti-jamming high accuracy, high safety and reliability, low cost and small size.

18 Claims, 3 Drawing Sheets

U.S. PATENT DOCUMENTS

| | | | | |
|---|---|---|---|---|
| 6,320,193 B1 * | 11/2001 | Morrison et al. | ............ | 250/393 |
| 6,418,189 B1 | 7/2002 | Scafer | ......................... | 378/57 |
| 6,795,522 B2 | 9/2004 | Nishide et al. | ................. | 378/4 |
| 7,050,533 B2 | 5/2006 | Heismann et al. | ............. | 378/53 |
| 7,092,485 B2 | 8/2006 | Kravis | ......................... | 378/57 |
| 2005/0084063 A1 * | 4/2005 | Heismann et al. | ............. | 378/53 |
| 2006/0234902 A1 | 10/2006 | Zhu et al. | .................... | 378/54 |

FOREIGN PATENT DOCUMENTS

| CN | 1439338 | 9/2003 |
|---|---|---|
| CN | 1779444 | 5/2006 |
| GB | 2420619 | 5/2006 |
| GB | 2420683 | 5/2006 |

OTHER PUBLICATIONS

Search and Examination Report for Application Serial No. GB0624581.5.

* cited by examiner

METHOD AND DEVICE FOR SECURITY-INSPECTION OF LIQUID ARTICLES WITH RADIATIONS

FIELD OF THE INVENTION

The present invention is related to the field of radiation detection, and particularly, to the method and device for quick security-inspection of liquid articles with radiations.

BACKGROUND OF THE INVENTION

The present application is claims priority of Chinese patent application Serial No. 200610127652.7, filed Sep. 5, 2006, the content of which is hereby incorporated by reference in its entirety.

Since 9/11 in U.S., security-inspection of aviation is becoming more and more emphasized. Besides traditional security-inspection of packs, security-inspection of the liquid articles carried by passengers is added. Accordingly, means and methods of a quick security-inspection of the liquid articles in packs are in dire need.

Nowadays, there are four types of detection methods used in security-inspection of liquid articles, including the chemical method, the electromagnetic method, the neutron detection method and the radiation detection, method, as follows:

1) The chemical method can be subdivided into the odor identification method, the ion scanning explosive detection method and the substance analysis. The odor identification in practical applications often fails to implement detection because of sealed and packaged conditions of liquid articles. The ion scanning explosive detection method is known for its high sensitivity, but with high false alarm rate, it suffers from the effects of background environment. The substance analysis is of high precision and high accuracy, but this method needs a certain period of time to analyze the sample, which cannot meet the demands of on-site quick detection.

2) The electromagnetic method works in an active measurement manner. It distinguishes liquid articles from each other according to their dielectric constants in the electromagnetic field. The electromagnetic method is easily subjected to severe effects of metal packages or other thick material packages. As a result, the electromagnetic method is limited in the case of complex package materials.

3) The use of the neutron, detection method will leave residual radiation remaining in the detected liquid due to the effect of "neutron activation". Furthermore, the radiation shielding is complicate true to neutrons' strong perforation, and the apparatus has to take a large area, so the method is not suitable for application in the security-inspection systems of civil aviation.

4) Currently, most of the security-inspection apparatuses of civil aviation are radiation apparatuses. In these apparatuses, the X-ray. 2D imaging technology and the three-dimensional CT technology are mostly adopted. These technologies, which are mainly used for security-inspection of packs, fail to accomplish the security-inspection of liquid articles in packs.

The X-ray 2D imaging technology acquires two-dimensional projection images by integrating three-dimensional information of articles to be detected along X-ray's direction. These images show difference in the form of grayscale or pseudo-color, to give the operator a vivid display. However, the X-ray 2D imaging technology is in defect of one-dimensional information of objects, so the detection of liquid articles is suffering from severe affection of shapes and sizes of the liquid articles.

The three-dimensional CT technology is the extension and application of CT technology. The CT technology was applied in the diagnostics first, which was implemented by conducting a multi-angle projection of respective slices of an article. By using a computer to reconstruct the multi-angle projection data of respective slices, reconstructed images were obtained. The information of the different attenuation coefficients in the reconstructed images was displayed in the form of different grayscales, by which the inner differences of the articles were displayed. With the development of the CT technology, the industrial CT for the nondestructive inspection and the package CT for the security-inspection were put into use, with the goal remaining to be acquiring the slice images of the inner difference of articles. Therefore, with the traditional X-ray 3D imaging technology for thee liquid articles, only the slice images with no differences can be seen, Thus, it is difficult for the security-inspection devices of the CT type to gain popularity, for their high cost and bulkiness, as a result of the wide range of the articles that can be detected by them.

To sum up, for the quick detection of the liquid articles the chemical method, the electromagnetic method and the neutron detection method are not suitable for quick security-inspection. By using the X-ray 2D imaging technology and the three-dimensional CT technology, grayscale images or pseudo color images with contrast are acquired, but these images cannot work as sufficient evidence fear the security inspection of the liquid articles.

SUMMARY OF THE INVENTION

In order to overcome the disadvantages in the existing technologies, an object of the invention is to provide a method as well as a device for security-inspection of liquid article using radiations, which can conduct a quick detection and get quantitative information of the liquid articles to be detected, without destroying the outer packages.

On the first aspect of the invention, the invention provided a method for security-inspection of liquid articles with radiations, comprising the following steps: acquiring initial environmental information; emitting radiation beams to transmit through the liquid articles; receiving the radiation beams through the liquid articles to form multi-angle projection data; then based on the original environment information and the uniformity of the liquid articles, computing a radiation absorption coefficient of the liquid articles by an inverse operation of the multi-angle projection data; finally comparing the radiation absorption coefficient with the preset data to get the relevant information of the liquid articles.

According to an embodiment of the invention, the original environment information comprises geometry boundary information of the liquid articles to be detected.

According to an embodiment of the invention, the geometry boundary information was obtained by the radiogram technology or, the scan imaging technology.

According to an embodiment of the invention, the liquid articles to be detected exhibit uniformity to radiations.

On the other aspect of the invention, it provided a device for security-inspection of liquid articles with radiations, which comprises the following parts: a radiation source for emitting radiation beams; a carrier mechanism to carry the liquid articles to be detected so as to have the radiation beams transmit through; a detection and collection appliance to acquire both initial environmental information and the multi-angle projection data of the liquid articles; and a computer data processor. The processor comprises means of computing radiation absorption coefficients of the liquid articles by an inverse operation of the multi-angle projection data, constrained by the original environment information and the uniformity of the liquid articles, and also means of comparing the radiation absorption coefficient with the preset data to get the relevant information of the liquid articles.

According to an embodiment of the invention, the radiation source is an X-ray machine (tube) or an isotope source According to an embodiment of the invention, there should be one or more radiation sources.

According to an embodiment of the invention, the energy of the radiation source is adjustable.

According to an embodiment of the invention, the detection and collection appliance is in the integral form of a detector and a data collector.

According to an embodiment of the invention, the detector is a solid detector a liquid detector, a gas detector or a semiconductor detector According to an embodiment of the invention, there is one or more detectors.

According to an embodiment of the invention, the detector is in a form of one-dimensional array or two-dimensional array.

According to an embodiment of the invention, the detector has the energy switching function.

According to an embodiment of the invention, the detector operates in the (current) integral mode or the pulse (counting) mode.

According to an embodiment of the invention, the multi-angle projection data is obtained by rotating the liquid articles to be detected or rotating the radiation source with the detection and collection appliance.

According to an embodiment of the invention, the multi-angle projection is obtained by increasing the amount of the projection angles or mounting the detector with an offset of ¼ size of a detector unit.

According to an embodiment of the invention, the computer data processor conducts the comparison by adopting predetermined identification algorithm.

According to an embodiment of the invention, the coordination of the radiation source, the detection and collection, appliance, the carrier mechanism and the computer data processor is controlled by the scan controller.

The device of the invention is advantageous in taking small area, of high accuracy, high safety and reliability besides easy shielding. The present invention is adapted to the security-inspection or aviation fields and other important sites.

BRIEF DESCRIPTION OF THE DRAWINGS

The features and advantages of the invention can be more clarified from the following detailed descriptions for the accompanying drawings. Wherein.

DETAILED DESCRIPTION OF THE PREFERRED EMBODIMENTS

Figure 1:
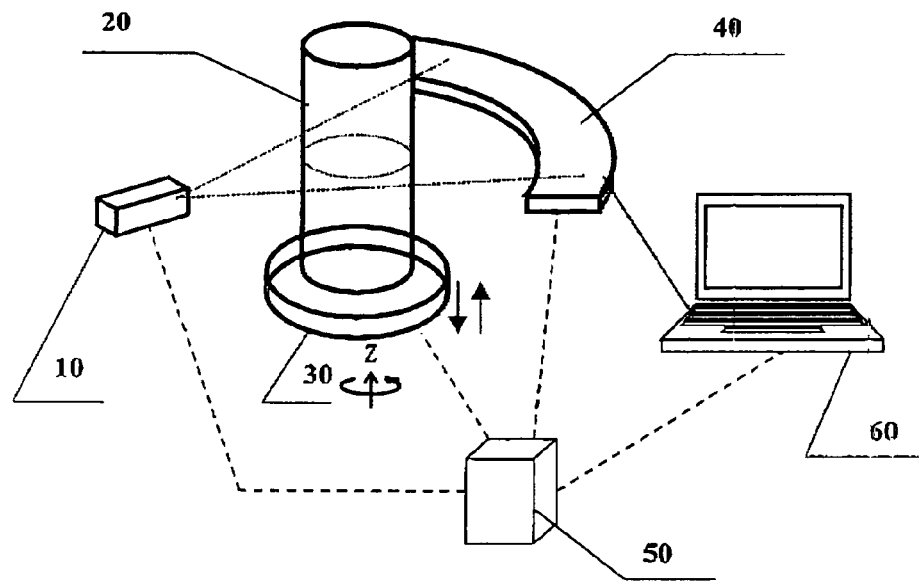
FIG. 1 is a schematic diagram of a detection device according to an embodiment of the invention.

The preferred embodiment of the invention will now be described more fully hereinafter with reference to the accompanying drawings. In the drawings the same reference numerals are used for denoting the same or similar components that are shown in different figures. For clarify, the detailed description of the known function and structure incorporated herein will be omitted, which would otherwise weaken the subject of the invention.

FIG. 1 is a schematic diagram of the structures of an inspection device according to an embodiment of the invention.

As shown in FIG. 1, the detection device according to the invention comprises a radiation source 10 for emitting radiations for detection, e.g. a X-ray machine or a isotope (X-ray or γ-ray source) source; a carrier mechanism 30, which carries the liquid articles to be detected 20, can rotate around axis Z thereof, and can ascend or descend to take the liquid articles 20 into the detection area, thereby the radiations emitted by the radiation source 10 can transmit through the liquid articles 20; a detection and collection appliance 40, an integrated module of a detector and a data collector, which is used to detect the radiations transmitted through the liquid articles 20 to acquire analog signals, and convert the analog signals into digital signals, and hence output the scanning data of the liquid articles 20; a scan controller 50, which controls each component of whole system so that they operate synchronously; and a computer data processor 60 for processing the, data collected by the data collector and outputting detection results.

As shown in FIG. 1, the radiation source 10 is placed at one side of the carrier mechanism 30 carrying the liquid articles to be detected 20, while the detection and collection appliance 40 is placed at the other side of the carrier mechanism 30. The detection and collection appliance 40 comprises a detector and a data collector for acquiring the initial environmental information and the multi-angle projection data of the liquid articles 20. The data collector has a signal amplifying and formation circuit, which operates under (current) integration mode or pulses (counting) mode. The detection and collection appliance 40 has its data output cable connected with the computer data processor 60 to store the collected data into a database.

Figure 2:
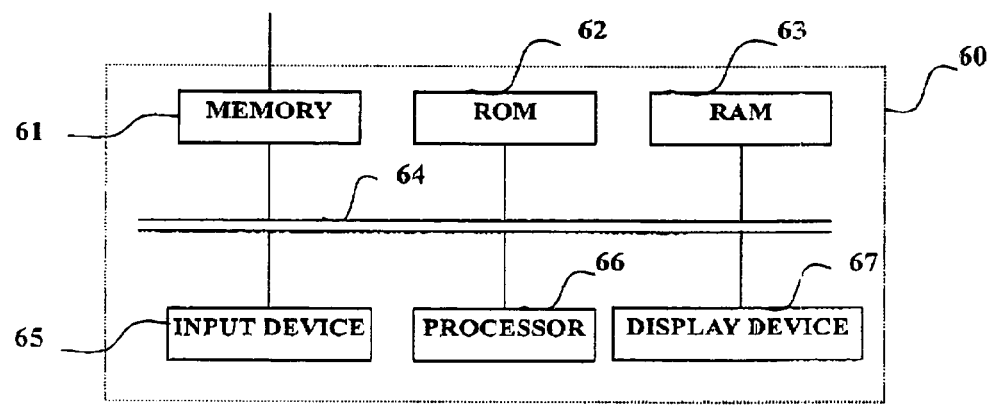
FIG. 2 shows a structure diagram of the computer data processor in the inspection device of FIG. 1.

FIG. 2 shows a structure diagram of the computer data processor 60 of FIG. 1. As shown in FIG. 2, the data collected by the data collector are stored in the memory 61. The configuration data and programs of the computer data processor are stored in the ROM (Read Only Memory) 62. The RAM (Random Access Memory) 63 is used for temporarily storing various data during the operating procedure of the processor 66. Besides, computer programs and a pre-created database are also stored in the memory 61 for data processing. The database stores various relevant parameters of known liquid articles, such as radiation absorption coefficient, density and etc, to compare with the radiation absorption coefficients of the liquid articles 20 computed by the processor 66. There is an internal bus 64 that connects the memory 61, the ROM 62, the RAM 63, the input device 65, the processor 66 and the display den isle 67 together.

After the user inputs operation commands through the input device 65 such as keyboards and mouse, the instruction code of the computer programs will instruct the processor 66 to perform predetermined data processing algorithm. After the processing results are obtained, they will be displayed on the display device 67 such as LCD, or redirected in the form of a hard copy.

Figure 3:
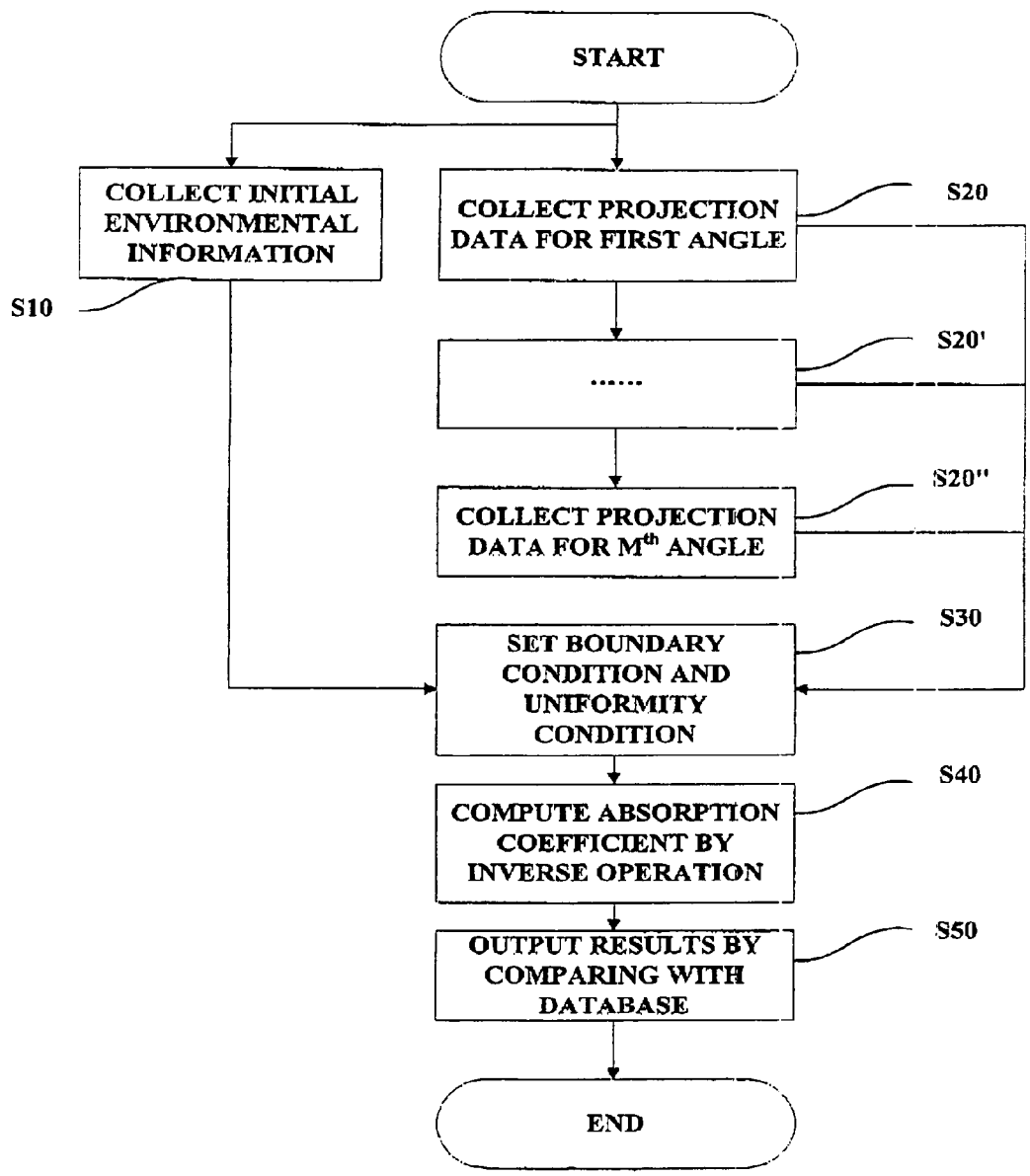
FIG. 3 shows a flow chart of the detection method according to an embodiment of the invention.

FIG. 3 shows the flow chart of a detection method according to an embodiment of the invention. As shown in FIG. 3, at step S10, the liquid articles to be detected 20 is placed on the carrier mechanism 30. When an operator sends out the command of starting a scan, the scan controller 50 controls the radiation source 10 to emit radiations, and controls the carrier mechanism 30 to ascend and descend so as to enter the detection area constituted by the X-ray source 10 and the detector. At the same time, radiation beams are emitted from the radiation source 10 and transmit through the liquid articles to be detected 20. The scan controller 50 controls the detection and collection appliance 40 to receive the radiations transmitted through the liquid articles 20, to acquire initial environmental information of the liquid articles, such as the geometry boundary information, etc. The geometry boundary information can be obtained by the X-ray radiographic technique or by X-ray scan imaging technology. The X-ray scan imaging technology can adopt translating mode, rotating mode or spiral mode.

Besides, in the above procedures, the obtained initial environmental information of the liquid articles to be detected 20 contains the size of package, the material of package, the volume ratio of package to liquid articles, and so on. These information and radiation absorption coefficients of various liquid articles can be pre-classified by using neural network recognition algorithm to form a database. In the real detection procedure, the detection of the liquid articles 20 is implemented by comparing the measured features with the features in the database.

Thereafter, at step S20, the carrier mechanism 30 rotates under the control of the scan controller 50. When the carrier mechanism, 30 reaches the first angle, radiations will be emitted from the radiation source 10 to transmit through the liquid articles to be detected 20. The detection and to collection appliance 40 receives the transmitted radiations to obtain the projection data of the first angle, which is denoted as a 1×N dimensional vector $g_1$ and stored in the memory 61 of the computer data processor 60, wherein N is the number of the detection units of one row in the detector.

At step S20', the carrier mechanism 30 continues rotating under the control of the scan controller 50. When the carrier mechanism 30 reaches the second angle, radiations will be emitted from the radiation source 10 to transmit through the liquid article 20. The detection and collection appliance 40 receives the transmitted radiations to obtain the projection data of the second angle, which is denoted as 1×N dimensional vector $g_2$ and stored in the memory 61 of the computer data processor 60.

The above steps are repeated in this manner. In step S20", the carrier mechanism 30 continues rotating under the control of the scan controller 50. When the carrier mechanism 30 reaches the $M^{th}$ angle, the projection data for $M^{th}$ angle is obtained, which is denoted as 1×N dimensional vector $g_M$ and stored in the memory 61 of the computer data processor 60. After the above scan procedure, the multi-angle projection data of the liquid articles 20 is obtained, which is denoted as an M×N dimensional vector g. Thereby, the multi-angle projection data of the liquid article to be detected 20 can be sequentially acquired for one slice.

Herein, in order to increase multi-angle projection data, the amount of angle projection can be increased during the scanning, or the detector is mounted with an offset of ¼ size of one detection unit of the detector.

Suppose that the linear attenuating coefficient (the absorption coefficient) of the liquid article to be detected 20 is expressed as an I-dimensional vector f, wherein I is the dimension of discretized pixels of the liquid article. Based on the interaction between X-ray and substance, according to the Bill's Law, we can get:

$$g_1 = \exp(-H_1 f)$$

$$g_2 = \exp(-H_2 f)$$

$$g_M = \exp(-H_M f) \quad (1)$$

Wherein the $H_1, \ldots, H_M$ each represents an N×I system matrix, whose element $H_{nj}$ reflects the contribution of the discrete pixel j in the object image under the corresponding angle, to the signal collected by the $n_{th}$ detector. $H_1 \ldots H_M$ each is a single sparse matrix, which is determined by practical design of the scanning system. For example, these matrices can be determined by pre-computing and then being stored in the memory 61, or through a real time computation according to the temporal system parameters. Thus, the linear attenuating coefficient information of the liquid articles can be obtained through the inverse operation with regard to the formula (1).

The inverse operation is an inverse process of normal operation. The process of normal operation is that the original signal emitted by radiation source attenuates when transmitting through the liquid articles 20 and the detector receives the attenuated radiation signal. Accordingly, an inverse operation is to compute the information of radiation attenuation by the liquid articles on the basis of the signal received by the detector.

However, during the detection procedure of liquid articles, because the inverse operation is an ill-conditioned problem, other information needs to be incorporated, e.g. the geometry boundary information of the liquid articles to be detected 20, which is obtained at the former step S10, so as to improve the validity and stability of the solution.

At step S30, the boundary condition and uniformity condition for the inverse operation are set on the basis of the initial environmental information obtained in step S10, which contains the geometry boundary information of the liquid article 20. The space shape of the liquid articles can be expressed as a bounded function. The geometry boundary information of the liquid articles 20 can be determined by the above X-ray radiographic technology or X-ray scan imaging technology, thereby the valid active region $\Omega$ can be defined, which is $f_i = 0$, for $i \notin \Omega$. The introduction of the boundary condition can speed up the solution, and to some extent ameliorate its ill-condition. Secondly, as the target object of the detection system is the liquid part, the scanned object can be divided into two parts, i.e. the liquid region $\Omega_l$ and the non-liquid region $\Omega_n$. For the uniformity of the liquid part, $f_i$ = smooth function, for $i \in \Omega_l$, will be lo obtained. The smooth function is characterized by that both the whole variance in the liquid region $\Omega_l$ and the local fluctuation in the non-liquid region $\Omega_n$ are limited. The use of the liquid articles uniformity greatly optimizes the extraction of the liquid article information, and improves the robustness of the system.

It is to be noted that the liquid articles having uniformity denotes those solutions, suspending liquids or emulsions that absorb the radiations uniformly. For example, in the above sense, the milk and the porridge etc are also liquid articles of uniformity, namely, the uniformity of these liquid articles will be exhibited when they absorb the radiation.

Therefore, at step S40, with the geometry boundary condition of the liquid articles 20 being the boundary condition and the uniformity of the liquid articles being the condition of convergence, using the above formula (1), the computer data processor 60 computes to get the radiation absorption coefficient of the liquid article 20. The valid radiation absorption coefficient of the liquid articles then can be worked out on the basis of the obtained statistical characteristics of the pixels within the region $\Omega_l$.

Thereafter, at step S50, the computer data processor 60 outputs the relevant information of the liquid article to be detected 20, by comparing the computed radiation absorption coefficient with those of the known liquids in the database.

For example, the radiation absorption coefficient of alcohol is −280, if the detected result for an unknown liquid article falls into the range of −270 to −290, this unknown liquid article in all probability is alcohol. Afterwards, the identification information of the detected liquid article will be shown on the display device 67 or directly printed out.

At the above step S40, the Bayesian method can be adopted to compute the radiation absorption coefficient of the liquid article 20 with the geometry boundary information and the uniformity as conditions. Also the non-statistical method can be adopted, wherein first solve the above formula (1) to obtain a preliminary radiation absorption coefficient, then after optimizing using the boundary condition and uniformity, estimate the linear attenuation coefficient of the liquid article 20 on the basis of distribution of $f_i$, for $i \in \Omega_1$, to improve the viability and the stability of the computation. The computation of the radiation absorption coefficient with the Bayesian method and the non-statistical method will be described below as examples.

[An example of computation of the linear absorption coefficient of liquid article with the Bayesian method]

1. Determine the target function:

$$\Phi(f) = \Phi_1(g; f) + \lambda P(f) \qquad (2)$$

Wherein $\Phi_1(g; f)$ is a likelihood function determined by the noise characteristics of the collected data, $P(f)$ is the metric of the uniformity for $f_1 \in \Omega_1$, e.g. $P(f) = -\text{variance}(f)|_{f \in \Omega}$, $\lambda$ is a regulation parameter preset empirically;

2. Solve $\hat{f}$ arg max$[\Phi(f)]$ using the numerical optimization method. During the process of solution, keep $f_i=0$, for $i \notin \Omega$;

3. Calculate the probability distribution $p(\mu_{liquid})$ of $f \in \Omega_1$ to get the linear absorption coefficient of the liquid article, e.g. $\mu_{liquid} = \text{mean}(f)|_{f \in \Omega_1}$, or $\mu_{liquid} = \text{arg max}(p(f))|_{f \in \Omega_1}$.

[An example of computation of the linear absorption coefficient of liquid article with the non-statistic method]

1. Acquire a preliminary estimate of the radiation absorption coefficient f by an analytic method, e.g. filter-back-projection reconstructing method or ART method;

2. Compute the uniformity of $f_i \in \Omega_1$ a) If the preset uniformity demand is satisfied, say, the local variance is lower than a certain threshold, then acquire the absorption coefficient of the liquid article on the basis of the statistical characteristics of $f \in \Omega_1$ such as $\mu_{liquid} = \text{mean}(f)|_{f \in \Omega_1}$.

b) If the uniformity demand is not satisfied, then conduct a boundary condition processing and a smoothing processing with regard to the radiation absorption coefficient f to acquire f'. Compare the orthographic projection of the processed f' with the collected data g, analyze the difference between again to reconstruct and modify f, and then return step 2.

During the implementation of the non-statistical method, the operational speed and precision can be adjusted by setting different uniformity demands. In some extreme cases, the absorption coefficient of liquid article can be obtained just by one step, without iteration.

Besides, at the above step S10, if the liquid article 20 is of a sandwiched structure or layered e.g. it has two layers. The geometry boundary information of these two layers can be obtained using the above method, respectively, then conduct the same subsequent procedures with regard to the liquid article of the respective layers, and finally output the identification information of the two types of liquid articles, which serves as the ultimate identification information of the detected liquid article 20.

For example, in the case of a two-layer liquid article, the liquid article region comprises the first liquid article region $\Omega_{1A}$ and the second liquid article region $\Omega_{1B}$. The linear attenuation coefficient of the first liquid article region $\Omega_{1A}$ is denoted as $f_A$, the linear attenuation coefficient of the second liquid article region $\Omega_{1B}$ is denoted as $f_B$. Then $f_A$=smooth function 1, for $A \in \Omega_{1A}$, $f_B$=smooth function 2, for $B \in \Omega_{1B}$.

Thus, the above-described step S10~S50 are conducted with regard to the first liquid article region $\Omega_{1A}$ and the second liquid article region $\Omega_{1B}$, respectively As mentioned above, based on the information such as the i of package, the material of package, the size ratio of the package to the liquid article, making use of the recognition algorithms such as the ANM (Artificial Neural Network), SVM (Support Vector Machine), BNN (Bayesian Neural Network), a classification table for the known various liquid articles can be established and stored into a database. As stated above, at steps S10 and S40, after acquiring the initial environmental information as well as the radiation absorption coefficient of the liquid article 20, the classification of the liquid article 20 in the database can hence be determined with the same neural network recognition algorithm, thereby the identification information of the liquid article 20 can be obtained.

In this embodiment of the invention, the scanning is implemented by rotating the detected liquid article 20. By means of scanning, both the volume and the cost of the device are reduced. However, another manner of scanning, that the detected liquid article 20 stays still while the radiation source 10 with the detection and collection appliance 40 rotates, can also be adopted.

Besides, the radiation source 10 may comprise one or more X-ray machines, as well as one or more isotope sources, and the radiation energy of the X-ray machines is adjustable. In the case that the radiation source 10 comprises a plurality of X-ray machines or isotope sources, there may be the same number of detectors as the X-ray machines or isotope sources, and these X-ray machines or isotope sources are set correspondingly. Herein, the detectors may be gas collectors, liquid detectors, solid detectors or semiconductor detectors, and may have an energy switching function. Besides, the detectors can work under the mode of one-dimensional array or two-dimensional arrays, i.e. the line array detector or the area array detector.

Figure 4:
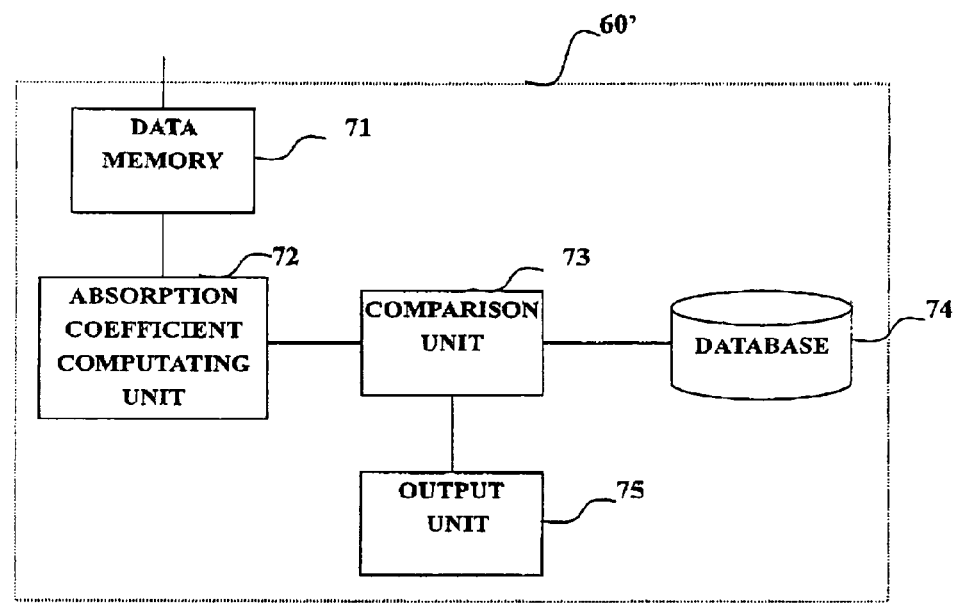
FIG. 4 shows a functional block diagram of the computer data processor in the inspection device of FIG. 1.

The computation procedure of the radiation absorption coefficient and the acquiring procedure of the identification information of the detected liquid article 20 are described above in the form that the computer data processor 60 runs the programs containing the predetermined data processing algorithm. However, the computer data processor 60 may be embodied in other forms. FIG. 4 is a functional block diagram of the computer data processor 60 of the inspection device of FIG. 1.

As shown in FIG. 4, as another example of the computer data processor, this computer data processor 60' comprises the following: a data memory 71, which stores the original environment information and the multi-angle projection data and etc, such as the system matrices $H_1, \ldots, H_M$ to describe the system property; the database 74, which stores the absorption coefficients of various liquid articles or other characteristic information, as well as a database of the classification table of various liquid articles to be used for the comparison of the checking procedure; an absorption coefficient calculation unit 72, which calculates the radiation absorption coefficient of the detected liquid article 20 based on formula (1), under the condition of uniformity of the liquid article, on the basis of the initial environmental information stored in the data memory 71 such as the geometry boundary information of liquid article, and the multi-angle projection data; a comparison unit 73, which compares the radiation coefficient of the liquid article 20 computed by the absorption coefficient computing unit 72 with those stored beforehand to determine the useful identification information of the liquid article 20; a output unit 75 such as a display or other output device, for presenting the identification information acquired by the comparison unit 73 to the operator.

Although exemplary embodiments of the present invention have been described hereinabove, it should be clear to those skilled in the field that any variations and/or modifications of the basic inventive concepts will still fall within the scope of the present invention, as defined in the appended claims.

What is claimed is:

1. A method for security-inspection of liquid articles with radiations comprising the steps of:
    acquiring initial environmental information comprising geometry boundary information of the liquid articles that are inspected;
    emitting radiation beams, each beam having the same, single energy to transmit through the liquid articles;
    receiving the radiation beams transmitted through the liquid articles to form multi-angle projection data;
    computing a radiation absorption coefficient of the liquid articles by the inverse operation of the multi-angle projection data, based on the initial environmental information and the uniformity of the liquid articles;
    comparing the radiation absorption coefficient with preset data to get relevant information of the liquid articles that are inspected.

2. The method of claim 1 wherein the geometry boundary information is obtained by radiographic technology or scan imaging technology.

3. The method of claim 1, wherein the geometry boundary information is obtained by radiographic technology or scan imaging technology.

4. The method of claim 1, wherein the liquid articles that are inspected exhibit uniformity with regard to radiation attenuation.

5. A device for security-inspection of liquid articles with radiations comprising:
    a radiation source for emitting radiation beams, each beam having the same, single energy;
    a carrier mechanism for carrying the liquid articles so as to have the radiation beams transmit through;
    a detection and collection means for acquiring original environment information comprising geometry boundary information of the liquid articles that are inspected and multi-angle projection data of the liquid articles to be detected; and
    a computer data processor, wherein
    the computer data processor comprises:
        means for computing radiation absorption coefficient of the liquid articles that are inspected by inverse operation of the multi-angle projection data, wherein the original environment information and the uniformity of the liquid articles being limiting conditions; and
        means for comparing the radiation absorption coefficients with preset data to get relevant parameters of the liquid articles that are inspected.

6. The device of claim 5 wherein the radiation source is an X-ray source or an isotope source.

7. The device of claim 6, further comprising one or more radiation sources.

8. The device of claim 6, wherein the energy of the radiation source is adjustable.

9. The device of claim 5, wherein the detection and collection appliance is integrally formed of a detector and a data collector.

10. The device of claim 9, wherein the detector is a solid detector, a liquid detector, a gas detector or a semiconductor detector.

11. The device of claim 9, further comprising one or more detectors.

12. The device of claim 9, wherein the detector is in the form of a one-dimensional array or a two-dimensional array.

13. The device of claim 9, wherein the detector has an energy switching function.

14. The device of claim 9, wherein the detector operates under integration mode or pulse mode.

15. The device of claim 9, wherein the multi-angle projection data is obtained by rotating the liquid articles to be detected or rotating the radiation source and the detection and collection appliance.

16. The device of claim 9, wherein the multi-angle projection data is obtained by increasing the amount of projection angles or mounting the detector with an offset of ¼ size of a detector unit.

17. The device of claim 5, wherein the computer data processor conducts the comparison by adopting a predetermined identification algorithm.

18. The device of claim 5, wherein radiation source, the detection and collection means, the carrier mechanism and the computer data processor are coordinated under the control of a scan controller.

* * * * *

UNITED STATES PATENT AND TRADEMARK OFFICE
CERTIFICATE OF CORRECTION

PATENT NO.       : 7,634,055 B2
APPLICATION NO.  : 11/634330
DATED            : December 15, 2009
INVENTOR(S)      : Hu et al.

It is certified that error appears in the above-identified patent and that said Letters Patent is hereby corrected as shown below:

Title Page, item (57), line 13, Delete the last sentence "Comparing with the prior art, the present invention is not subjected to affection of cuter package of the liquid article, and is advantageous of high anti-jamming high accuracy, high safety and reliability, low cost and small size." and insert --Comparing with the prior art, the present invention is not subjected to affection of outer package of the liquid article, and is advantageous of high anti-jamming, high accuracy, high safety and reliability, low cost and small size.--

Signed and Sealed this

Sixteenth Day of March, 2010

David J. Kappos
*Director of the United States Patent and Trademark Office*